United States Patent
Hannemann et al.

(10) Patent No.: US 10,512,417 B2
(45) Date of Patent: Dec. 24, 2019

(54) IMAGING APPARATUS AND METHOD FOR DISPLAYING POSITION INFORMATION

(71) Applicant: Siemens Healthcare GmbH, Erlangen (DE)

(72) Inventors: Thilo Hannemann, Erlangen (DE); Bastian Rackow, Erlangen (DE)

(73) Assignee: SIEMENS HEALTHCARE GMBH, Erlangen (DE)

(*) Notice: Subject to any disclaimer, the term of this patent is extended or adjusted under 35 U.S.C. 154(b) by 210 days.

(21) Appl. No.: 15/225,864

(22) Filed: Aug. 2, 2016

(65) Prior Publication Data
US 2017/0049529 A1 Feb. 23, 2017

(30) Foreign Application Priority Data
Aug. 21, 2015 (DE) .......................... 10 2015 216 052

(51) Int. Cl.
*A61B 5/00* (2006.01)
*A61B 5/055* (2006.01)
(Continued)

(52) U.S. Cl.
CPC ................ *A61B 5/055* (2013.01); *A61B 5/00* (2013.01); *A61B 6/032* (2013.01); *A61B 6/0492* (2013.01); *G01R 33/283* (2013.01); *G01R 33/543* (2013.01)

(58) Field of Classification Search
CPC ....... A61B 6/032; A61B 90/37; A61B 90/361; A61B 6/0492; A61B 5/055;
(Continued)

(56) References Cited

U.S. PATENT DOCUMENTS

2004/0017882 A1* 1/2004 Misawa ............... A61B 6/4441
378/4
2004/0082852 A1* 4/2004 Cherek ............... A61B 6/0457
600/427
(Continued)

FOREIGN PATENT DOCUMENTS

CN 1476813 A 2/2004
CN 102805636 A 12/2012
(Continued)

OTHER PUBLICATIONS

German Office Action and English translation thereof dated May 2, 2016.
(Continued)

*Primary Examiner* — Ruth S Smith
(74) *Attorney, Agent, or Firm* — Harness, Dickey & Pierce, P.L.C.

(57) ABSTRACT

A method is for displaying position information relating to a position of a region of interest of a patient relative to an examination unit of an imaging apparatus. A first examination plane is assignable to the examination unit and a camera is disposed relative to the examination unit such that, via a lens of the camera, three non-collinear reference points lying in a first reference plane parallel to the first examination plane are mapped to three collinear first image points lying on a first line. In an embodiment, the method includes capturing a camera image of the region of interest via the camera; displaying a positioning image, the positioning image including the camera image; and displaying first marking information relating to a position of the first line in the positioning image.

23 Claims, 7 Drawing Sheets

(51) Int. Cl.
*A61B 6/04* (2006.01)
*A61B 6/03* (2006.01)
*G01R 33/28* (2006.01)
*G01R 33/54* (2006.01)

(58) Field of Classification Search
CPC ..... A61B 2090/373; A61B 90/00; A61B 6/00; A61B 6/03; A61B 6/04; A61B 5/00; G06K 9/32; G01R 33/283; G01R 33/543
USPC .......................................................... 600/407
See application file for complete search history.

(56) References Cited

U.S. PATENT DOCUMENTS

| | | | |
|---|---|---|---|
| 2004/0122311 A1* | 6/2004 | Cosman | A61B 6/5247 600/427 |
| 2006/0241400 A1* | 10/2006 | Bucholz | A61B 5/0064 600/424 |
| 2009/0088621 A1 | 4/2009 | Xu et al. | |
| 2009/0251709 A1 | 10/2009 | Kindlein | |
| 2009/0292200 A1 | 11/2009 | Kindlein et al. | |
| 2015/0063535 A1 | 3/2015 | Gatayama et al. | |
| 2016/0074004 A1 | 3/2016 | Braun et al. | |
| 2016/0092078 A1 | 3/2016 | Braun et al. | |

FOREIGN PATENT DOCUMENTS

| | | |
|---|---|---|
| CN | 104352246 A | 2/2015 |
| DE | 69433588 T2 | 2/2005 |
| DE | 69833881 T2 | 12/2006 |
| DE | 102008012496 A1 | 9/2009 |
| DE | 102008025014 A1 | 11/2009 |
| DE | 102013200135 A1 | 7/2014 |
| DE | 102014216718 A1 | 2/2016 |
| DE | 102014218558 A1 | 3/2016 |
| DE | 102014219667 B3 | 3/2016 |
| JP | 2013180024 A | 9/2013 |
| WO | WO-20160026758 A1 | 2/2016 |

OTHER PUBLICATIONS

German Decision to Grant and English translation thereof dated Nov. 18, 2016.
Chinese Office Action and English translation thereof dated Jan. 22, 2018.
Office Action for Chinese Patent Application No. 201610697246.8 dated Jul. 17, 2018 and English translation thereof.

* cited by examiner

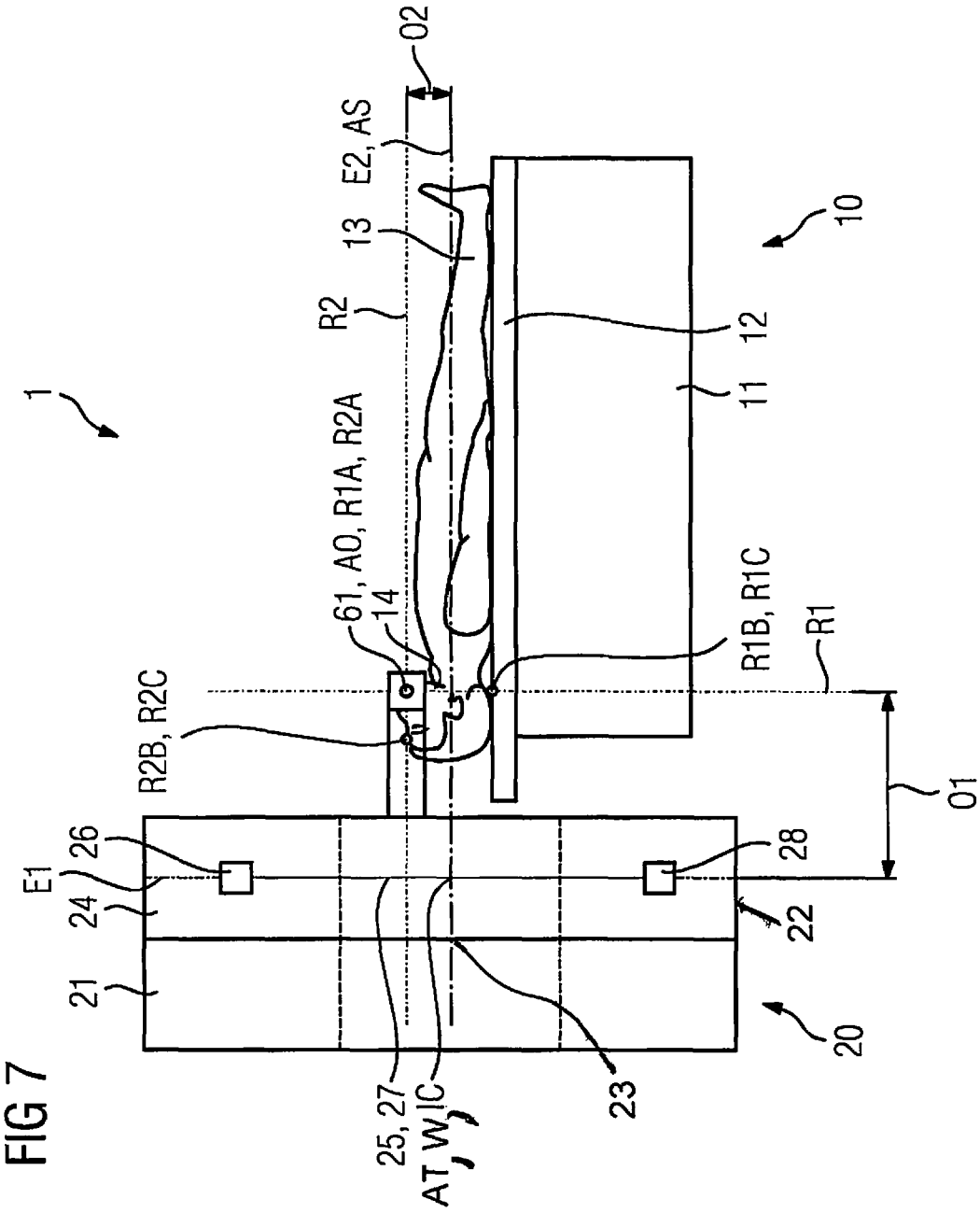

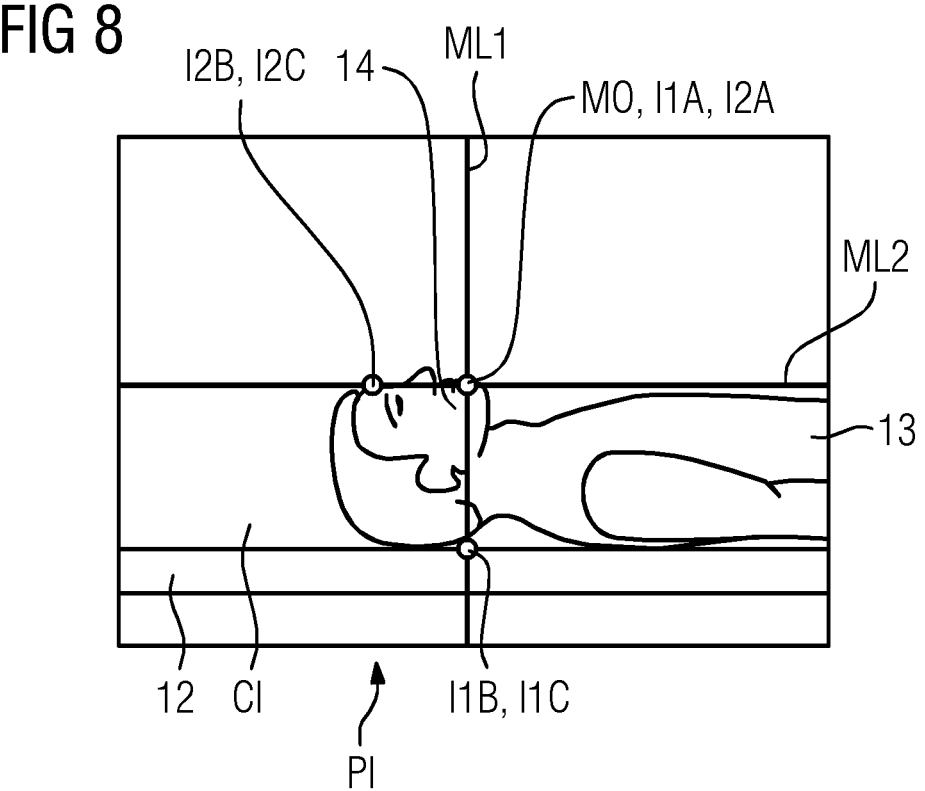

IMAGING APPARATUS AND METHOD FOR DISPLAYING POSITION INFORMATION

PRIORITY STATEMENT

The present application hereby claims priority under 35 U.S.C. § 119 to German patent application number DE 102015216052.1 filed Aug. 21, 2015, the entire contents of which are hereby incorporated herein by reference.

FIELD

At least one embodiment of the invention generally relates to a method for displaying position information relating to the position of a region of interest of a patient relative to an examination unit of an imaging apparatus. At least one embodiment of the invention also generally relates to a method for positioning a patient relative to an examination unit, and/or an imaging apparatus.

BACKGROUND

For examining a patient via an imaging apparatus, a position of a region of interest of the patient relative to an examination unit of the imaging apparatus is typically determined and/or adjusted. For this purpose the patient can, for example, be positioned relative to the examination unit such that a selected slice of the region of interest lies in an examination plane assignable, in particular assigned, to the examination unit. On the basis of such a position of the region of interest, a topogram and/or a conventional radiographic image, for example, can be obtained for planning the acquisition of an imaging data set.

The examination plane can be visually indicated e.g. via a laser localizer. By way of a patient positioning device, the patient can be transferred such that the selected slice comes to lie in the examination plane. For this purpose, an operator can view a position of the selected slice relative to the visually indicated examination plane and adjust the transfer of the patient accordingly. The selected slice can be in particular a slice with which the taking of the topogram and/or the acquisition of the imaging data set begins. The selected slice can be in particular a slice which delimits the region of interest in respect of a scanning direction in which the patient is moved during the taking of the topogram and/or acquisition of the imaging data set. The extent of the region of interest along the scanning direction can be adjusted e.g. by numerical input and/or selection of a length via a user interface.

For taking the topogram and acquiring the imaging data set, the region of interest is typically disposed in an acquisition area of the imaging apparatus, wherein the acquisition area is constituted by a tunnel-shaped aperture and the examination plane runs through the acquisition area. Viewing the position of the selected slice relative to the visually indicated examination plane can be awkward for the operator. Particularly if the selected slice is close to or in the examination plane, it may be necessary for the operator to lean into the tunnel in order to be able to identify the position of the selected slice.

SUMMARY

At least one embodiment of the invention enables improved positioning of a patient relative to an examination unit of an imaging apparatus.

At least one embodiment is directed to a method and at least one embodiment is directed to an imaging apparatus. The claims relate to advantageous embodiments of the invention.

A method according to at least one embodiment of the invention is for displaying position information relating to a position of a region of interest of a patient relative to an examination unit of an imaging apparatus. A first examination plane is assignable, in particular assigned, to the examination unit. A camera is disposed relative to the examination unit such that, by way of a lens of the camera, three non-collinear first reference points lying in a first reference plane parallel to the first examination plane are mapped to three collinear first image points lying on a first line. A camera image of the region of interest is obtained via the camera. A positioning image is displayed, wherein the positioning image includes the camera image. First marking information relating to a position of the first line in the positioning image is displayed.

An embodiment of the invention provides that the examination unit is designed to acquire an imaging data set. In particular, the examination unit can have a radiation source and a detector. In the case of computed tomography machine, the radiation source can be an X-ray source and the detector an X-ray detector. In the case of a magnetic resonance tomography machine, the radiation source can be an RF antenna and the detector the same RF antenna or another RF antenna.

With the method according to an embodiment of the invention for positioning a patient relative to an examination unit of an imaging apparatus, an embodiment of the inventive method is carried out to display position information relating to a position of a region of interest of a patient relative to an examination unit of an imaging apparatus, wherein the patient is placed in a preparatory position on a patient positioning device.

In the preparatory position, a first slice of the region of interest of the patient lies in the first reference plane and/or a second slice of the region of interest of the patient lies in the second reference plane. A control command is issued, wherein the control command causes the patient to be transferred via the patient positioning device from the preparatory position to an examination position on the basis of the distance information. In the examination position, the first slice lies in the first examination plane and/or the second slice lies in the second examination plane.

An embodiment of the invention provides that, in the preparatory position, one or two or three of the three first reference points are located in the first slice and/or that, in the preparatory position, one or two or three of the three second reference points are located in the second slice of the region of interest. An embodiment of the invention provides that the second slice delimits the region of interest in respect of a scanning direction in which the patient is moved for taking a topogram and/or acquiring an imaging data set, and/or that the second slice is a slice with which the taking of the topogram and/or acquisition of the imaging data set begins.

The imaging apparatus according to an embodiment of the invention has an examination unit, a camera, a positioning image display unit and a first marking information display unit. A first examination plane is assignable, in particular assigned, to the examination unit. The camera is designed to capture a camera image of a region of interest of a patient, wherein the camera is disposed relative to the examination unit such that, via a lens of the camera, three non-collinear first reference points lying in a first reference plane parallel to the first examination plane are mapped to three collinear first image points lying on a first line. The positioning image display unit is designed to display a positioning image, wherein the positioning image shows the camera image. The marking information display unit is designed to display first marking information relating to a position of the first line relative to the camera image.

BRIEF DESCRIPTION OF THE DRAWINGS

The invention will now be described once again in greater detail with reference to the accompanying drawings using example embodiments. The representation in the figures is schematic and highly simplified and not necessarily to scale, wherein FIG. 7 shows a side view of the imaging apparatus according to the fourth embodiment of the invention, FIG. 8 shows an illustration of the positioning image and of the first marking information according to the fourth embodiment of the invention.

DETAILED DESCRIPTION OF THE EXAMPLE EMBODIMENTS

Figure 1:
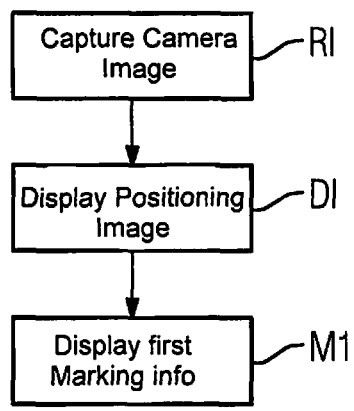
FIG. 1 shows a flow chart of a method according to a first embodiment of the invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

A method according to at least one embodiment of the invention is for displaying position information relating to a position of a region of interest of a patient relative to an examination unit of an imaging apparatus. A first examination plane is assignable, in particular assigned, to the examination unit. A camera is disposed relative to the examination unit such that, by way of a lens of the camera, three non-collinear first reference points lying in a first reference plane parallel to the first examination plane are mapped to three collinear first image points lying on a first line. A camera image of the region of interest is obtained via the camera. A positioning image is displayed, wherein the positioning image includes the camera image. First marking information relating to a position of the first line in the positioning image is displayed.

An embodiment of the invention provides that the position information comprises the positioning image and/or the first marking information. An embodiment of the invention provides that the positioning image is the camera image. Alternatively or in addition to the camera image, the positioning image can show image information based on further processing of the camera image. The image information can relate e.g. to the contours of the patient and/or of the region of interest.

An embodiment of the invention provides that the position of the first line in the positioning image corresponds to a position of the first line relative to the camera image. An embodiment of the invention provides that the positioning image and the first marking information are displayed such that the positioning image and the first marking information are simultaneously in an operator's field of vision.

In this way the operator can view the camera image of the region of interest and the position of the first line relative to the camera image simultaneously. The inventors have realized that, by the disposition of the camera and the first reference plane, a relationship can be established between the position of the first line relative to the camera image of the region of interest and the position of the region of interest relative to the examination unit. Here a first relationship between the position of the first line relative to the camera image and a position of the region of interest relative to the first reference plane can be established. As the first reference plane is parallel to the first examination plane, a second relationship can be established between the position of the region of interest relative to the first reference plane and the position of the region of interest relative to the first examination plane.

The inventors propose displaying the position information relating to the position of the region of interest relative to the examination unit using the positioning image and the first marking information. The position information in particular enables the operator to determine and/or adjust the position of the region of interest relative to the examination unit.

The position of the region of interest can be understood as meaning in particular a position of a first slice of the region of interest. The first slice is preferably parallel to the first examination plane and the first reference plane. An embodiment of the invention provides that the first slice delimits the region of interest with respect to a scanning direction in which the patient moves during the taking of a topogram and/or acquisition of an imaging data set and/or that the first slice is a slice with which the taking of a topogram and/or acquisition of the imaging data set begins.

The position of the first slice relative to the examination unit can be defined in particular by a distance of the first slice from the first examination plane and/or a distance of the first slice from the first reference plane. The position information enables the operator to ascertain, for example, whether the first slice lies in the first reference plane. The camera is disposed such that the image points of the first slice lie on the first line if the first slice lies in the first reference plane.

In addition, the position information enables the operator to ascertain in which direction and/or by what distance the position of the patient has to be changed in order to implement a preparatory position in which the first slice of the patient lies in the first reference plane. A preparatory position of the patient can therefore be implemented in which the first slice lies in the first reference plane. Starting from the preparatory position, an examination position in which the first slice lies in the first examination plane can be implemented by one or more translatory movements of the patient.

For taking the topogram and/or acquiring the imaging data set, radiation is typically generated via a radiation source which can interact with the region of interest and with a detector. During the interaction with the region of interest, the radiation is modified and thus becomes the carrier of information relating to the region of interest. During the interaction with the detector, this information is acquired and/or provided in the form of an imaging data set. From the imaging data set, an image of the region of interest can be reconstructed using a reconstruction technique. Alternatively or in addition to the patient, an object can be examined by way of the imaging apparatus. Accordingly, the position information can alternatively or additionally relate to a position of a region of interest of the object relative to the examination unit.

An embodiment of the invention provides that the examination unit is designed to acquire an imaging data set. In particular, the examination unit can have a radiation source and a detector. In the case of computed tomography machine, the radiation source can be an X-ray source and the detector an X-ray detector. In the case of a magnetic resonance tomography machine, the radiation source can be an RF antenna and the detector the same RF antenna or another RF antenna.

According to an embodiment of the invention, a second examination plane can be assigned, in particular is assigned, to the examination unit, wherein the camera is disposed relative to the examination unit such that, by way of the lens, three non-collinear second reference points lying in a second reference plane parallel to the second examination plane are mapped to three collinear second image points lying on a second line, wherein second marking information relating to a position of the second line in the positioning image is displayed.

An embodiment of the invention provides that the position information comprises the second marking information. An embodiment of the invention provides that the position of the second line in the positioning image corresponds to a position of the second line relative to the camera image. An embodiment of the invention provides that the positioning image, the first marking information and the second marking information are displayed such that the positioning image, the first marking information and the second marking information are simultaneously in an operator's field of vision. In this way the operator can simultaneously view the camera image of the region of interest as well as the position of the first line and the position of the second line relative to the camera image. The inventors have realized that, by way of the disposition of the camera and the second reference plane, a relationship can be established between the position of the second line relative to the camera image of the region of interest and the position of the region of interest relative to the examination unit.

The first reference points and/or the second reference points can be, for example, points on a surface of the patient, in particular of the region of interest of the patient, and/or points on a surface of a patient positioning device. However, the first reference points and/or the second reference points need not necessarily be points on a surface of the patient, in particular of the region of interest of the patient, and/or points on a surface of a patient positioning device. For example, the first reference points and/or the second reference points can also be points on a surface of the camera lens. An embodiment of the invention provides that the first reference points and/or the second reference points are on the object side with respect to the camera lens.

A first reference point can simultaneously be a second reference point. A first image point can simultaneously be a second image point. An embodiment of the invention provides that each of the three first reference points is mapped to one of the three first image points and/or that each of the three second reference points is mapped to one of the three second image points. The three first reference points are in particular non-collinear if there can be no straight line on which the three second reference points lie. The first line can in particular be straight. The three second reference points are in particular non-collinear if there can be no straight line on which the three second reference points lie. The second line can in particular be straight.

A disposition of the camera such that, via the camera lens, the three non-collinear first reference points are mapped to the three collinear first image points can be implemented in particular using three first non-collinear adjustment points. A disposition of the camera such that, via the camera lens, the three non-collinear first reference points are mapped to the three collinear first image points and the three non-collinear second reference points are mapped to the three collinear second image points can be implemented in particular using three first non-collinear adjustment points and three second non-collinear adjustment points. A first adjustment point can simultaneously be a second adjustment point.

An adjustment point can be implemented e.g. using an adjustment marking on the imaging apparatus, in particular on a patient positioning device. An adjustment point can alternatively or additionally be implemented using an adjustment marking on an adjustment device which can be disposed in a predefined position relative to the examination unit, e.g. on the imaging apparatus. The three first adjustment points can be disposed in a non-collinear manner in the first reference plane parallel to the first examination plane. The first reference plane can therefore be defined by the three first adjustment points. The three second adjustment points can be disposed in a non-collinear manner in the second reference plane parallel to the second examination plane. The second reference plane can therefore be defined by the three second adjustment points.

The first adjustment points and/or second adjustment points are disposed relative to a patient positioning area provided for positioning the patient such that the first adjustment points and/or second adjustment points and at least part of the patient positioning area can be simultaneously captured via the camera. The camera can be disposed, e.g. by way of a supporting structure, on a ceiling and/or on a floor and/or a wall of the examination room in which the imaging apparatus is installed. Alternatively, the camera can be disposed, e.g. by way of a supporting structure, on the imaging apparatus. The disposition of the camera can be implemented in particular by appropriately adjusting and/or predefining one or more angles relating to the position of the camera relative to the first reference plane and/or the second reference plane. For example, the supporting structure can be designed to adjust the one or more angles. Alternatively or in addition, the supporting structure can be designed, for example, such that the camera can be disposed in a predetermined position on the supporting structure, wherein the one or more angles are predefined accordingly. The geometric parameters of such a supporting structure can be determined, for example, using the three first adjustment points and/or second adjustment points and/or calculated using a geometric model of the imaging apparatus and the camera.

According to an embodiment of the invention, the positioning image shows the first marking information and/or the second marking information. In this way the camera image and the first marking information and/or the second marking information are simultaneously displayed via the positioning image display unit. The operator can therefore comprehend the position information quickly and reliably.

An embodiment of the invention provides that the first line and/or a position of the first line in the positioning image is indicated by way of the first marking information and/or that the second line and/or a position of the second line in the positioning image is indicated by way of the second marking information. The first marking information and/or the second marking information can be displayed as part of the positioning image e.g. in addition to the camera image. This can be achieved e.g. by showing the first marking information and/or the second marking information superimposed on the positioning image and/or overlying the camera image.

An embodiment of the invention provides that the first marking information is displayed via a first marking device and/or via an image of a first marking device and/or that the second marking information is displayed via a second marking device and/or via an image of a second marking device. The first marking device and/or the second marking device can, for example, be disposed relative to the positioning image display unit such that, in the positioning image, a position of the first line is indicated via the first marking device and/or a position of the second line is indicated via the second marking device. For example, the positioning image display unit is designed as a screen and/or as a sub-area of a screen, wherein the first marking device and/or the second marking device is disposed on and/or relative to the screen, in particular at an edge of the screen.

An embodiment of the invention provides that the first marking information and/or the second marking information is part of the camera image. This can be achieved e.g. by a first marking device or a second marking device together with the region of interest being captured via the camera. For example, the first marking device can be disposed relative to the first reference plane and/or the second marking device can be disposed relative to the second reference plane such that the camera image shows an image of the first marking device and/or an image of the second marking device, wherein, in the positioning image, a position of the first line is indicated by way of the image of the first marking device and/or a position of the second line is indicated by way of an image of the second marking device.

According to an embodiment of the invention, the first marking information comprises a first marking line assigned to the first line and/or the second marking information comprises a second marking line assigned to the second line. The first marking line is in particular assigned to the first line if the position of the first marking line in the positioning image and/or the position of the first marking line relative to the camera image corresponds to the position of the first line relative to the camera image. This can be achieved e.g. by the first marking line being displayed overlaid, in particular superimposed, on the first line and/or the three first image points. The second marking line is in particular assigned to the second line if the position of the second marking line in the positioning image and/or the position of the second marking line relative to the camera image corresponds to the position of the second line relative to the camera image. This can be achieved e.g. by the second marking line being displayed overlaid, in particular superimposed, on the second line and/or the three second image points.

A simple 2D camera can be used as the camera. In particular, a 3D and/or depth camera is not required for the method according to the invention. The camera has a lens. Via the lens, in particular a point lying on an object side with respect to the lens can be optically mapped to an image point lying on an image point side with respect to the lens.

According to an embodiment of the invention, an optical axis of the lens intersects the first line and/or the second line. An embodiment of the invention provides that the camera is disposed relative to the examination unit such that the optical axis of the lens lies in the first reference plane and/or in the second reference plane. Disposing a camera in this way obviates the need for distortion correction of the camera image. A simple computer webcam, for example, can therefore be used directly as a camera, in particular without calibration measurements having to be carried out.

According to an embodiment of the invention, the second examination plane is disposed perpendicular and/or at a finite angle to the first examination plane. An embodiment of the invention provides that the first examination plane or the second examination plane is vertical or essentially vertical. An embodiment of the invention provides that the first examination plane or the second examination plane is horizontal or essentially horizontal. A plane is essentially vertical if the plane forms an angle of less than 30 degrees, in particular of less than 20 degrees, preferably of less than 10 degrees with a vertical plane. A plane is in particular essentially horizontal if the plane forms an angle of less than 30 degrees, in particular of less than 20 degrees, preferably of less than 10 degrees with a horizontal plane.

According to an embodiment of the invention, the examination unit has an isocenter located in the first examination plane and/or in the second examination plane. An embodiment of the invention provides that in particular the first examination plane is assignable, in particular assigned, to the examination unit if the examination unit has an isocenter located in the first examination plane. An embodiment of the invention provides that in particular the second examination plane is assignable, in particular assigned, to the examination unit if the examination unit has an isocenter located in the second examination plane. In particular, the position information can relate to a position of the region of interest relative to the isocenter.

The first examination plane is in particular assignable to the examination unit if the first examination plane is assigned to the examination unit.

The second examination plane is in particular assignable to the examination unit if the second examination plane is assigned to the examination unit.

According to an embodiment of the invention, the examination unit has a radiation source for producing radiation, wherein a central ray of the radiation lies in the first examination plane and/or in the second examination plane. An embodiment of the invention provides that the radiation is fan shaped, wherein at least in one operating state of the imaging apparatus one plane of the fan lies in the first examination plane and/or in the second examination plane. The first examination plane and/or the second examination plane can be in particular a scan plane of the imaging apparatus.

An embodiment of the invention provides that the first examination plane and/or the second examination plane is perpendicular or parallel to another plane, wherein the other plane is selected from the group consisting of a first plane, a second plane, a third plane, a fourth plane and a fifth plane. The first plane comprises the longitudinal axis of the patient's body. The second plane comprises a system axis of the imaging apparatus. The third plane is defined by a transfer plate of a patient positioning device. The fourth plane runs through a radiation source and/or a detector. The fifth plane is a rotation plane of a rotor on which a radiation source and/or a detector is disposed.

According to an embodiment of the invention, distance information relating to a first distance of the first reference plane from the first examination plane and/or a second distance of the second reference plane from the second examination plane is provided. An embodiment of the invention provides that the distance information comprises the first distance of the first reference plane from the first examination plane and/or the second distance of the second reference plane from the second examination plane.

The distance information can be provided e.g. by determining and/or setting the first distance of the first reference plane from the first examination plane and/or the second distance of the second reference plane from the second examination plane when disposing the camera. The first distance can be determined e.g. by measuring the distance of a first reference point or of a first adjustment point from the first examination plane. The first distance can be set e.g. by disposing the three first adjustment points in each case at a predetermined position having a predefined distance from the first examination plane. The second distance of the second reference plane from the second examination plane can be determined e.g. by measuring a distance of a second reference point or of a second adjustment point from the second examination plane. The second distance can be set e.g. by disposing the three second adjustment points in each case at a predetermined position having a predefined distance from the second examination plane.

An embodiment of the invention provides that the first distance is the distance of the first reference plane from the first examination plane and that the second distance is the distance of the second reference plane from the second examination plane. An embodiment of the invention provides that the first distance is referred to a first direction and/or that the second distance is referred to a second direction. An embodiment of the invention provides that the first direction and/or the second direction is selected from the group comprising a horizontal direction, a vertical direction, a direction of the longitudinal axis of the patient's body, a direction of the system axis of the imaging apparatus, a scanning direction in which the patient and/or the transfer plate is moved for taking a topogram and/or acquiring the imaging data set, and a feed direction of the transfer plate of the patient positioning device. The distance information can be retrievably stored e.g. in a storage device of a control device of the imaging apparatus and/or a storage device of a control unit of the patient positioning device.

With the method according to an embodiment of the invention for positioning a patient relative to an examination unit of an imaging apparatus, an embodiment of the inventive method is carried out to display position information relating to a position of a region of interest of a patient relative to an examination unit of an imaging apparatus, wherein the patient is placed in a preparatory position on a patient positioning device.

In the preparatory position, a first slice of the region of interest of the patient lies in the first reference plane and/or a second slice of the region of interest of the patient lies in the second reference plane. A control command is issued, wherein the control command causes the patient to be transferred via the patient positioning device from the preparatory position to an examination position on the basis of the distance information. In the examination position, the first slice lies in the first examination plane and/or the second slice lies in the second examination plane.

An embodiment of the invention provides that, in the preparatory position, one or two or three of the three first reference points are located in the first slice and/or that, in the preparatory position, one or two or three of the three second reference points are located in the second slice of the region of interest. An embodiment of the invention provides that the second slice delimits the region of interest in respect of a scanning direction in which the patient is moved for taking a topogram and/or acquiring an imaging data set, and/or that the second slice is a slice with which the taking of the topogram and/or acquisition of the imaging data set begins.

Providing the distance information makes it possible in particular to carry out the transfer of the patient from the preparatory position to the examination position.

The control command can be issued and/or received e.g. in the form of a voltage and/or current pulse, a data packet or an instruction implemented in software. Issuing of the control command can be initiated e.g. by an operator by actuating a key. The key can be present e.g. in the form of hardware, in particular on the patient positioning device, on the imaging apparatus, in the examination room or in a control room, or in the form of software, in particular as a button in a user interface.

An embodiment of the invention provides that, alternatively or in addition to the issuing of the control command, a transfer of the patient via the patient positioning device from the preparatory position to the examination position is carried out on the basis of the distance information.

An embodiment of the invention provides that the control command causes the patient to be transferred from the preparatory position to the examination position via the patient positioning device on the basis of the distance information when the control command is issued to the patient positioning device.

An embodiment of the invention provides that the control command is issued via the control device and/or is received via the control unit. The control command can comprise e.g. the distance information and/or cause the distance information to be retrieved from a storage device via the control device and/or the control unit.

The control unit can be designed in particular to control the patient positioning device such that the transfer of the patient from the preparatory position to the examination position is carried out on the basis of the distance information when the control command is received by the control unit. In particular, the transfer is based on the distance information if, during the transfer, the patient is moved by the first distance in the first direction and/or by the second distance in the second direction.

The imaging apparatus according to an embodiment of the invention has an examination unit, a camera, a positioning image display unit and a first marking information display unit. A first examination plane is assignable, in particular assigned, to the examination unit. The camera is designed to capture a camera image of a region of interest of a patient, wherein the camera is disposed relative to the examination unit such that, via a lens of the camera, three non-collinear first reference points lying in a first reference plane parallel to the first examination plane are mapped to three collinear first image points lying on a first line. The positioning image display unit is designed to display a positioning image, wherein the positioning image shows the camera image. The marking information display unit is designed to display first marking information relating to a position of the first line relative to the camera image.

According to an embodiment of the invention, a second examination plane is assignable, in particular assigned, to the examination unit, wherein the camera is disposed relative to the examination unit such that, via a lens of the camera, three non-collinear second reference points lying in a second reference plane parallel to the second examination plane are mapped to three collinear second image points lying on a second line, wherein the imaging apparatus has a second marking information display unit which is designed to display second marking information relating to a position of the second line relative to the camera image.

According to an embodiment of the invention, the imaging apparatus has a distance information providing unit and a control command issuing unit. The distance information providing unit is designed to provide distance information relating to a first distance of the first reference plane from the first examination plane and/or a second distance of the second reference plane from the second examination plane. The control command issuing unit is designed to issue a control command, wherein the control command causes the patient to be transferred from the preparatory position to the examination position via a patient positioning device on the basis of the distance information.

According to an embodiment of the invention, the imaging apparatus has a patient positioning device designed to transfer the patient from the preparatory position to the examination position.

According to an embodiment of the invention, the imaging apparatus for carrying out the method according to the invention is designed to display position information relating to a position of a region of interest of a patient relative to an examination unit of an imaging apparatus, or, to carry out the method according to the invention, is designed to position a patient relative to an examination unit of an imaging apparatus. In particular, the capturing of the camera image via the camera, the displaying of the positioning image by way of the positioning image display unit, the displaying of the first marking information by way of the first marking information display unit, the displaying of the second marking information by way of the second marking information display unit, the providing of the distance information via the distance information providing unit, the issuing of the control command via the control command issuing unit and the transferring of the patient via the patient positioning device can be carried out.

At least one embodiment of the invention makes it possible, in particular, to dispense with a laser localizer. A solution, in at least one embodiment, offers various advantages in particular compared to a laser localizer which indicates a plane parallel to an examination plane outside the tunnel shaped aperture such that an operator can visually capture a position of the patient relative to the indicated parallel plane without having to lean inside the tunnel.

The advantage of the inventive solution, in at least one embodiment, over patient positioning via a visual light localizer is in particular that it is not necessary for the operator to be directly adjacent to the imaging apparatus. The positioning can be carried out on the basis of the positioning image and the first marking information and/or the second marking information. The positioning can therefore be carried out/controlled e.g. from a control room and/or via remote access via the Internet. Another advantage over a visual light localizer, in at least one embodiment, is that the patient is not irritated by the lasers of the visual light localizer, which is a problem particularly if the first slice and/or the second slice is in the vicinity of the patient's eyes.

An embodiment of the invention provides that the imaging apparatus is a medical imaging apparatus and/or that the imaging apparatus is selected from the group comprising a computed tomography machine, a single photon emission computed tomography machine (SPECT machine), a positron emission tomography machine (PET machine), a magnetic resonance tomography machine and combinations thereof. In particular, the imaging apparatus can have an X-ray machine, a C-arm X-ray machine, an ultrasound machine and similar. The imaging apparatus can also be a combination of a plurality of imaging and/or irradiation modalities, e.g. a PET-CT machine or a SPECT-CT machine. An irradiation modality can have, for example, an irradiation machine for therapeutic irradiation.

Within the scope of the invention, features which are described with reference to different embodiments and/or different claim categories (method, device, etc.) may be combined to produce further embodiments. In particular, the features, advantages and embodiments described with reference to the method according to the invention are also applicable to the imaging apparatus according to the invention and vice versa. In other words, the claims in question can also be further developed using the features described or claimed in connection with a method. Functional features of the method can be carried out by suitably designed components of the imaging apparatus. The term "unit" does not exclude the possibility that that the "unit" consists of a plurality of components which may also possibly be spatially distributed. The use of the indefinite article "a" or "an" does not exclude the possibility of a plurality of the features in question also being present.

The method and imaging apparatus described are merely embodiments of the invention. The invention may be varied by the person skilled in the art without departing from the scope of the invention in so far as it is specified by the claims.

FIG. 1 shows a flow chart of a method for displaying position information according to a first embodiment of the invention, wherein the position information relates to a position of a region of interest 14 of a patient 13 relative to an examination unit 26, 28 of an imaging apparatus 1, wherein a first examination plane E1 is assignable, in particular assigned, to the examination unit 26, 28, wherein a camera 61 is disposed relative to the examination unit 26, 28 such that, via a lens of the camera 61, three non-collinear reference points R1A, R1B, R1C lying in a first reference plane R1 parallel to the first examination plane E1 are mapped to three collinear first image points I1A, I1B, I1C lying on a first line. In step RI, a camera image CI of the region of interest 14 is captured via the camera 61. In step DI, a positioning image is displayed, wherein the positioning image PI has the camera image CI. In step M1, first marking information ML1 is displayed which relates to a position of the first line in the positioning image PI.

In the embodiments shown below, in particular refining features are described with reference to the previously explained embodiments in each case. Features that remain essentially the same, in particular steps and units, are provided with the same reference characters.

Figure 2:
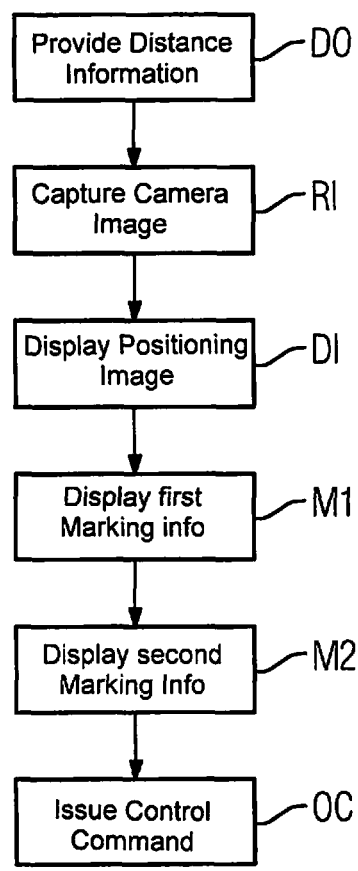
FIG. 2 shows a flow chart of a method according to a second embodiment of the invention.

FIG. 2 shows a flow chart of a method for positioning a patient 13 relative to an examination unit 26, 28 of an imaging apparatus 1 according to a second embodiment of the invention, wherein a second examination plane E2 is assignable, in particular assigned, to the examination unit 26, 28, wherein the camera 61 is disposed relative to the examination unit 26, 28 such that, via the lens, three non-collinear second reference points R2A, R2B, R2C lying in a second reference plane R2 parallel to the second examination plane E2 are mapped to three collinear second image points I2A, I2B, I2C lying on a second line. In step DO, distance information relating to a first distance O1 of the first reference plane R1 from the first examination plane E1 and/or a second distance O2 of the second reference plane R2 from the second examination plane E2 is provided. In step M2, second marking information ML2 relating to a position of the second line in the positioning image PI is displayed.

The second embodiment of the invention provides that the steps DO, RI, DI, M1 and M2 are executed, wherein the patient is placed in a preparatory position on a patient positioning device. In step OC, a control command is issued, wherein the control command causes the patient 13 to be transferred via the patient positioning device 10 from the preparatory position to an examination position on the basis of the distance information, wherein, in the examination position, the first slice lies in the first examination plane E1 and/or the second slice lies in the second examination plane E2.

Figure 3:
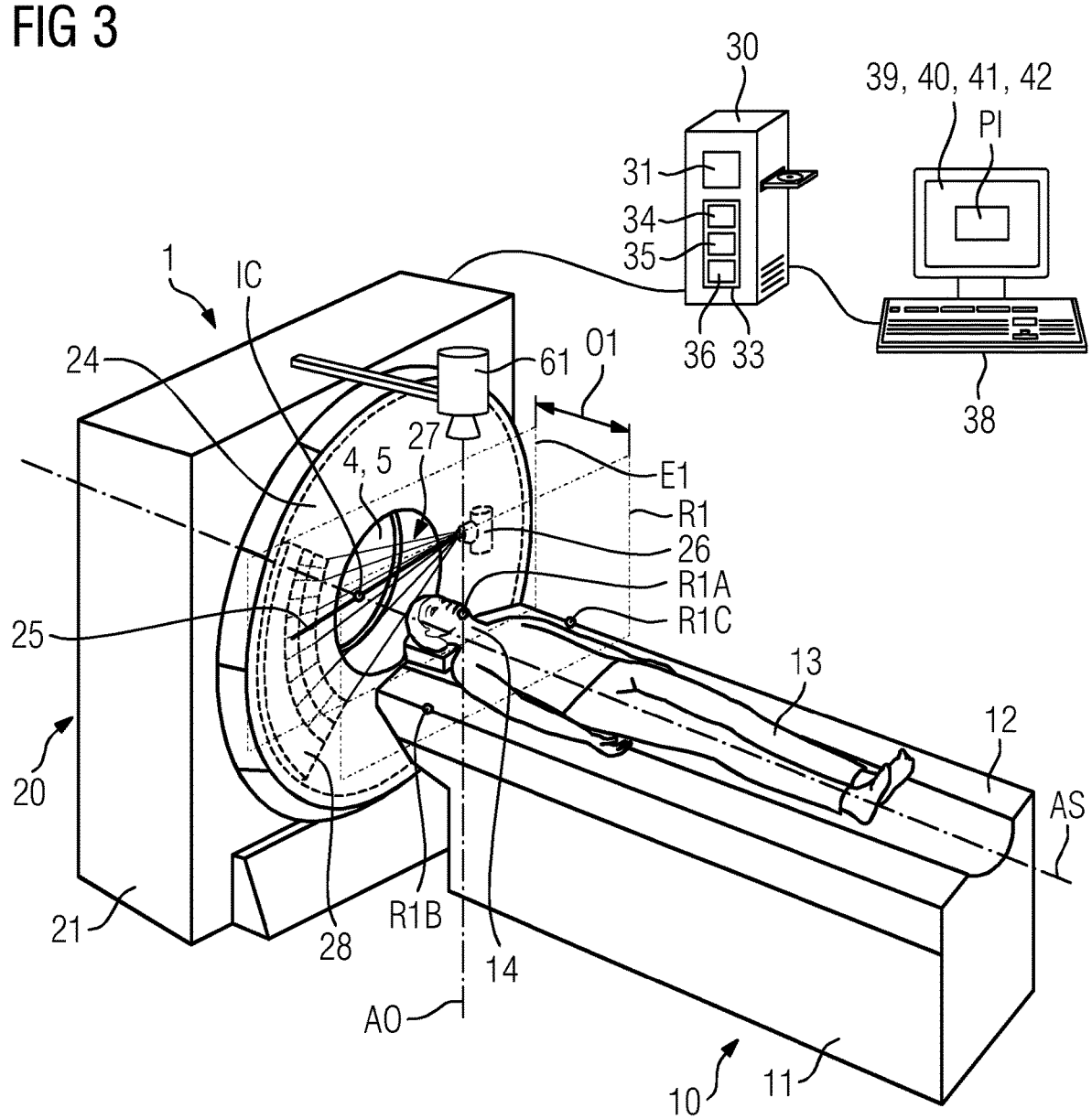
FIG. 3 shows a perspective view of an imaging apparatus according to a third embodiment of the invention.
Figure 4:
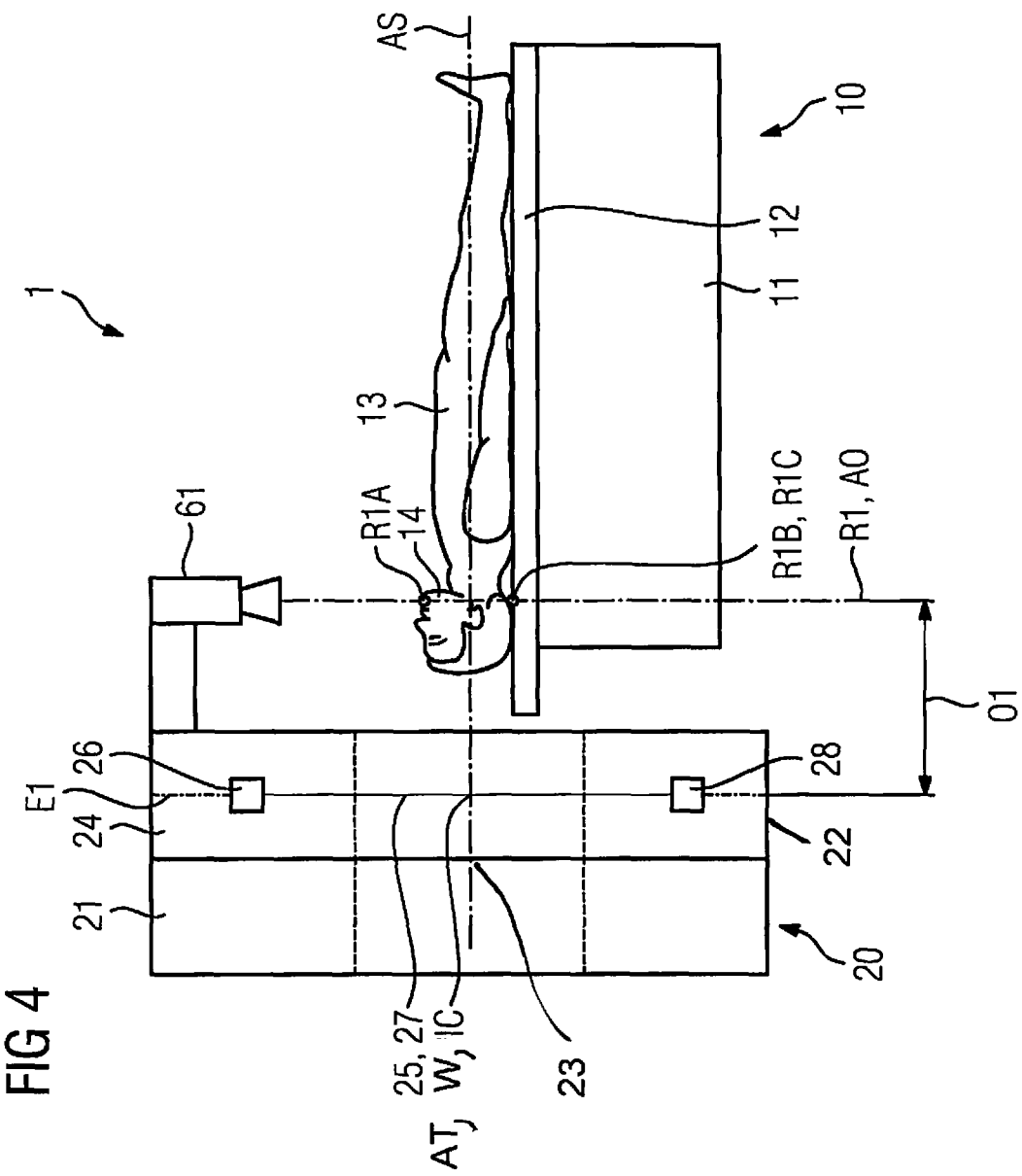
FIG. 4 shows a side view of the imaging apparatus according to the third embodiment of the invention.

FIG. 3 and FIG. 4 show an imaging apparatus 1 according to a third embodiment of the invention. Without limitation of the general inventive concept, a computed tomography machine 1 is shown as an example of an imaging apparatus 1. The third embodiment of the invention provides that the examination unit has a radiation source, in particular the X-ray source 26, and a detector, in particular the X-ray detector 28.

The imaging apparatus 1 has a gantry 20, an acquisition area 4, a patient positioning device 10 and an examination unit 26, 28.

The gantry 20 has a fixed support frame 21 and a rotor 24. The rotor 24 is rotatably mounted about a system axis AS via a pivot bearing device. The acquisition area 4 is formed by a tunnel-shaped opening 5 in the gantry 20. A region of interest of an object, in particular of the patient 13, can be disposed in the acquisition area 4. The patient positioning device 10 has a positioning table 11 and a transfer plate 12 for positioning the patient 13. Said transfer plate 12 is movably disposed on the positioning table 11 relative to the positioning table 11 such that the transfer plate 12 can be introduced into the acquisition area 4 in a longitudinal direction of the transfer plate 12.

The examination unit 26, 28 is designed to acquire the imaging data set. The examination unit 26, 28 has a radiation source 26 designed to emit radiation quanta, and a detector 28 designed to detect radiation quanta. The radiation quanta 27 can pass from the radiation source 26 to the region of interest and, after interacting with the region of interest, impinge upon the detector 28. In this way a projection profile of the region of interest can be obtained. The imaging data acquired by the examination unit 26, 28 is forwarded to the control device 30.

The radiation source 26 and the detector 28 are disposed on the rotor 24. The third embodiment provides that the first examination plane E1 is a rotation plane of the rotor 24. By rotation of the radiation source 26 and detector 28 about the acquisition area 4, at least one projection profile can be obtained for different dispositions of the radiation source 26 and detector 28 in respect of the region of interest 14 in each case. A plurality of projection profiles can form an imaging data set. The control device 30 is designed in particular for the storage and retrieval of imaging data in the form of projection profiles and/or in the form of an imaging data set. Based on an imaging data set, a tomographic image of the region of interest can be reconstructed via an image reconstruction device 34.

The imaging apparatus 1 has a control device 30, an input device 38 and an output device 39. The control device 30 is designed to control the imaging apparatus 1. The input device 38 is designed for entering control information, e.g. image reconstruction parameters and/or examination parameters. The output device 39 is designed to output control information and/or reconstructed images. The output device 39 has a screen. The output device 39 has the positioning image display unit 40 and the first marking information display unit 41. The positioning image PI and the first marking information ML1 are displayed in a sub-area of the screen of the output device 39.

The control device 30 has a storage device 31 and a data processing device 33. The storage device 31 is designed in particular to store distance information. The imaging apparatus 1 has an image reconstruction device 34 which is implemented in the form of software on a processor system of the data processing device 33. The processor system can be constituted e.g. by one or more co-operating microprocessors.

According to the third embodiment of the invention, the imaging apparatus 1 has a camera 61, a positioning image display unit 40 and a first marking information display unit 41. A first examination plane E1 is assignable, in particular assigned, to the examination unit 26, 28. The camera 61 is designed to record RI a camera image CI of a region of interest 14 of a patient 13, wherein the camera 61 is disposed relative to the examination unit 26, 28 such that, via a lens of the camera 61, three non-collinear reference points R1A, R1B, R1C lying in a first reference plane R1 parallel to the first examination plane E1 are mapped to three collinear first image points I1A, I1B, I1C lying on a first line.

The positioning image display unit 40 is designed to display DI a positioning image PI, wherein the positioning image PI shows the camera image CI. The first marking information display unit 41 is designed to display M1 first marking information ML1 relating to a position of the first line in the positioning image PI.

The point R1A lies on a surface of the patient 13. The points R1B and R1C lie on a surface of the transfer plate 12 of the patient positioning device 10. The reference point R1A lies on the optical axis AO of the lens of the camera 61. The optical axis AO intersects the first line and lies in the first reference plane. The examination unit 26, 28 has an isocenter IC which is located in the first examination plane E1. The examination unit 26, 28 has a radiation source 26 for producing radiation, wherein a central ray 25 of the radiation which runs from the radiation source 26 to the detector 28 lies in the first examination plane E1. The third embodiment of the invention provides that the first examination plane E1 is vertical.

The third embodiment of the invention provides that the camera 61 is disposed above the patient positioning device 10 and is aligned perpendicularly downward onto the patient 13. The third embodiment of the invention provides that the camera 61 is disposed in a position suitable or intended for disposing a laser localizer for indicating a plane parallel to the first examination plane. Alternatively, the camera 61 can be disposed somewhat higher up. The position of the camera 61 in respect of the system axis AS can be selected depending on the vertical position of the camera 61 such that a view of the camera 61 into the tunnel-shaped aperture 5 is impaired as little as possible by the gantry 20. In the case of a camera 61 disposed comparatively higher in respect of the vertical direction, it is therefore advantageous to dispose the camera 61 at a comparatively greater distance from the tunnel-shaped aperture 5 in respect of the system axis AS.

It must therefore be ensured in particular that a slice of the region of interest 14 which is located between the first reference plane R1 and the first examination plane E1 with the transfer plate 12 fully moved out, cannot under any circumstances be placed in the first reference plane R1 by moving the transfer plate 12 out. In this respect it is advantageous for the camera 61 to be disposed as near as possible to the first examination plane E1. On the other hand it is desirable that the camera 61 be located at a distance from the patient 13 such that an aesthetically pleasing image of the patient 13 can be implemented even without an extreme wide-angle lens. The camera 61 is preferably disposed such that a camera image CI of a section of the patient 13 can be obtained, wherein the section extends on both sides with respect to the first reference plane R1 up to a distance of at least 10 centimeters, in particular at least 20 centimeters, from the first reference plane R1.

The imaging apparatus 1 has a distance information providing unit 36 and a control command issuing unit 35. The third embodiment of the invention provides that both the distance information providing unit 36 and the control command issuing unit 35 are implemented in the form of software on the processor system of the data processing device 33. The distance information providing unit 36 is designed to provide DO distance information relating to a distance O1 of the first reference plane R1 from the first examination plane E1. The control command issuing unit 35 is designed to issue OC a control command, wherein the control command causes the patient 13 to be transferred from a preparatory position to an examination position via a patient positioning device 10 on the basis of the distance information. FIG. 3 and FIG. 4 show the patient in a preparatory position in which the first slice of the region of interest 14 lies in the first reference plane R1. The third embodiment of the invention provides that, in the preparatory position, the first reference point R1A is located in the first slice of the region of interest 14. In the examination position, the first slice of the region of interest 14 lies in the first examination plane E1. The patient positioning device 10 is designed to transfer the patient 13 from the preparatory position to the examination position.

The third embodiment of the invention provides that the imaging apparatus 1 is designed in particular to carry out the method according to the first embodiment of the invention.

Figure 5:
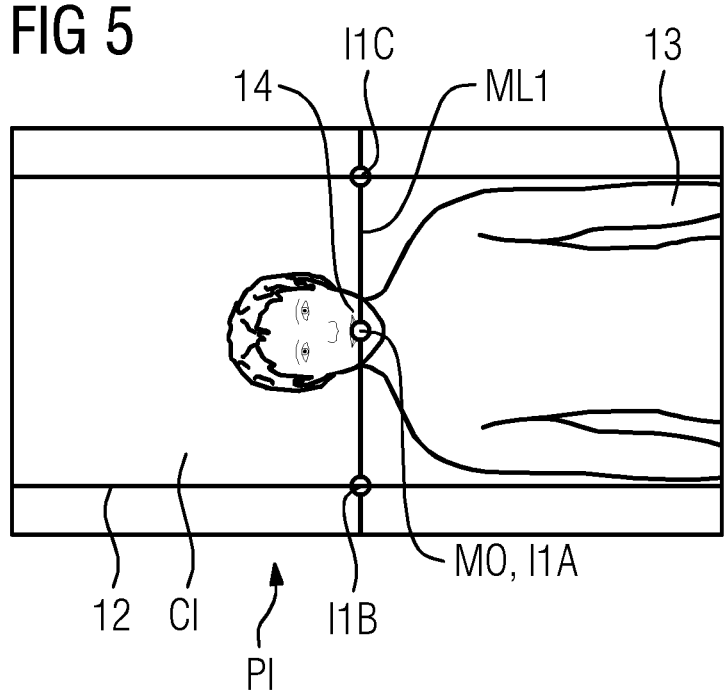
FIG. 5 shows an illustration of the positioning image and of the first marking information according to the third embodiment of the invention.

FIG. 5 shows an illustration of the positioning image PI and of the first marking information ML1 according to the third embodiment of the invention. The positioning image PI shows the camera image CI of the region of interest 14, wherein the camera image CI has been obtained via the camera 61. The first marking information ML1 relates to a position of a first line on which the three collinear first image points I1A, I1B and I1C lie in the positioning image PI. The first reference point R1A is mapped to the first image point I1A. The first reference point R1B is mapped to the first image point I1B. The first reference point R1C is mapped to the first image point I1C.

The third embodiment of the invention provides that the position information comprises the positioning image PI and that the positioning image PI and the first marking information ML1 are displayed such that the positioning image PI and the first marking information ML1 are simultaneously in an operator's field of vision. The positioning image PI has the first marking information ML1. The first marking information ML1 comprises a first marking line ML1 assigned to the first line. The first marking information ML1 is displayed in addition to the camera image CI as part of the positioning image PI. The first marking information ML1 is displayed overlaid on the positioning image PI and superimposed on the camera image CI. The first marking line ML1 is assigned to the first line.

The third embodiment of the invention provides that the position of the center point MO of the camera image CI corresponds to the position of the optical axis AO, that the center point MO of the camera image CI lies on the first marking line ML1, and that the camera 61 is disposed relative to the examination unit 26, 28 such that the optical axis AO lies in the first reference plane R1. The image point I1A lies on the center point MO.

The position of the first marking line ML1 corresponds to a position of the first line and a position of the first reference plane R1. The first marking line ML1 is shown superimposed on the three first image points I1A, I1B and I1C. This makes it possible to position the region of interest 14 relative to the first reference plane R1 and relative to the first examination plane E1.

Figure 6:
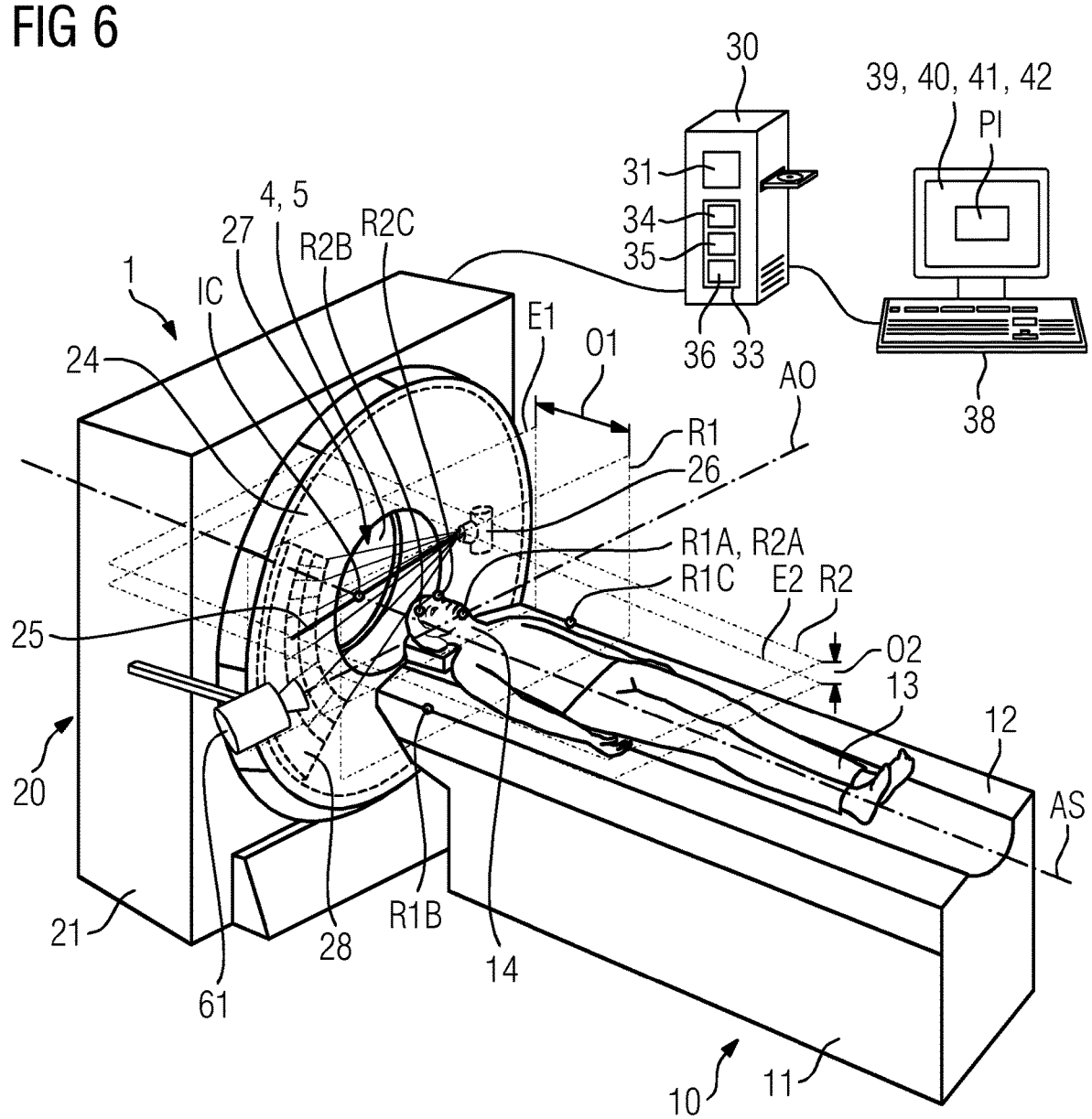
FIG. 6 shows a perspective view of an imaging apparatus according to a fourth embodiment of the invention.

FIG. 6 and FIG. 7 show an imaging apparatus 1 according to a fourth embodiment of the invention. According to the fourth embodiment of the invention, a second examination plane E2 is assignable, in particular assigned, to the examination unit 26, 28, wherein the camera 61 is disposed relative to the examination unit 26, 28 such that, via the lens, three non-collinear second reference points R2A, R2B, R2C lying in a second reference plane R2 parallel to the second examination plane E2 are mapped to three collinear second image points I2A, I2B, I2C lying on a second line. The points R2A, R2B and R2C lie on the surface of the patient 13. The point R2A is identical to the point R1A. The second examination unit 26, 28 has an isocenter IC located in the first examination plane E1 and in the second examination plane E2. The second examination plane E2 is disposed perpendicular to the first examination plane E1. The first examination plane E1 is vertical and the second examination plane E2 horizontal. According to the fourth embodiment of the invention, the output device 39 has the second marking information display unit 42. The positioning image PI, the first marking information ML1 and the second marking information are displayed on a sub-area of the screen of the output device 39.

The fourth embodiment of the invention provides that the imaging apparatus 1 is designed in particular to carry out the method according to the second embodiment of the invention. The imaging apparatus 1 according to the fourth embodiment of the invention allows in particular vertical positioning of the patient 13. In particular, the height at which the patient 13 is positioned can therefore be adjusted to the isocenter IC.

FIG. 6 and FIG. 7 show the patient 13 in a preparatory position in which the first slice of the region of interest 14 lies in the first reference plane R1 and in which the second slice of the region of interest 14 lies in the second reference plane R2. The fourth embodiment of the invention provides that, in the preparatory position, the first reference point R1A is in the first slice of the region of interest 14 and that, in the preparatory position, the three second reference points R2A, R2B and R2C are in the second slice of the region of interest 14. The fourth embodiment provides that, in the examination position, the first slice of the region of interest 14 lies in the first examination plane E1 and the second slice of the region of interest 14 lies in the second examination plane E2.

The fourth embodiment of the invention provides that the camera 61 is disposed relative to the examination unit 26, 28 such that the optical axis AO of the lens lies in the first reference plane R1 and in the second reference plane R2. The fourth embodiment of the invention provides that the camera 61 is disposed in a position suitable and/or intended for disposing a laser localizer for indicating a plane parallel to the second examination plane E2. The fourth embodiment of the invention provides that the camera 61 is disposed laterally with respect to the patient positioning device 10. The laterally disposed camera 61 is advantageous in particular for patients 13 who are placed in a lateral position. In addition to the laterally disposed camera 61, another camera can optionally be used, wherein, as shown in FIG. 3 and FIG. 4, the other camera is disposed above the patient. The other camera is advantageous in particular for horizontal positioning of the patient 13.

FIG. 8 shows an illustration of the positioning image PI, the first marking information ML1 and the second marking information ML2 according to the fourth embodiment of the invention. The second marking information ML2 relates to a position of a second line in the positioning image PI, on which line the three collinear second image points I2A, I2B and I2C lie. The second reference point R2A is mapped to the second image point I2A. The second reference point R2B is mapped to the second image point I2B. The second reference point R2C is mapped to the second image point I2C.

The fourth embodiment of the invention provides that the positioning image PI, the first marking information ML1 and the second marking information ML2 are displayed such that the positioning image PI, the first marking information ML1 and the second marking information ML2 are simultaneously in an operator's field of vision. The positioning image PI shows the first marking information ML1 and the second marking information ML2. The second marking information ML2 comprises a second marking line ML2 assigned to the second line. The second marking information ML2 is displayed in addition to the camera image CI as part of the positioning image PI. The second marking information ML2 is overlaid on the positioning image PI and shown superimposed on the camera image CI. The second marking line ML2 is assigned to the second line.

The fourth embodiment of the invention provides that the position of the center point MO of the camera image CI corresponds to the position of the optical axis AO, that the center point MO of the camera image CI lies on the first marking line ML1 and on the second marking line ML2, and that the camera 61 is disposed relative to the examination unit 26, 28 such that the optical axis AO lies in the first reference plane R1 and in the second reference plane R2. The point I2A is identical to the point I1A. The image point I2A lies on the center point MO.

The position of the second marking line ML2 corresponds to a position of the second line and a position of the second reference plane R2. The second marking line ML2 is shown superimposed on the three second image points I2A, I2B and I2C. This enables the region of interest 14 to be positioned relative to the second reference plane R1 and relative to the second examination plane E1.

The gantry 20 can optionally have a tilting frame 22, wherein the tilting frame 22 is mounted via a tilting device 23 so as to tilt relative to the fixed support frame 21 about a tilt axis AT, wherein the rotor 24 and the pivot bearing device are disposed on the tilting frame 22. The tilt axis AT is preferably horizontal and perpendicular to the system axis AS. The first examination plane E1 and/or the second examination plane E2 can optionally be tilted together with the tilting frame 22 about the tilt axis AT by a tilt angle W from a first tilting frame position to a second tilting frame position.

In such a case, the distance information can be provided depending on the tilt angle W. For example, the first distance O1 of the first reference plane R1 from the first examination plane E1 and/or the second distance O2 of the second reference plane R2 from the second examination plane E2 can be determined and/or set for the first tilting frame position. From the first distance O1 and/or the second distance O2 for the first tilting frame position, a first distance O1 and/or a second distance O2 for the second tilting frame position can be calculated as a function of the tilt angle W, e.g. using a geometric model.

Moreover, in such a case, the first marking information ML1 and/or the second marking information ML2 can be displayed as a function of the tilt angle W. For example, the second marking line ML2 in the first tilting frame position can correspond to a horizontal second reference plane R2 and, for the second tilting frame position, be displayed rotated relative to the camera image CI by the tilt angle W such that the second marking line ML2 also corresponds to the horizontal second reference plane R2 in the second tilting frame position. Alternatively, the camera 61 can be rotated relative to the tilting frame 22 about the optical axis AO by the tilt angle W such that the second marking line ML2 also corresponds to the horizontal second reference plane R2 in the second tilting frame position.

In this way, for a camera 61 which is tilted together with the tilting frame 22, the first marking information ML1 and/or the second marking information ML2 or rather the disposition of the camera 61 in relation to a first reference plane R1 and/or a second reference plane R2 which is not tilted together with the tilting frame 22 can be adjusted as a function of the tilt angle W. Accordingly, for a camera 61 which is not tilted together with the tilting frame 22, the first marking information ML1 and/or the second marking information ML2 or rather the disposition of the camera 61 in relation to a first reference plane R1 and/or a second reference plane R2 which is tilted together with the tilting frame 22 can be adjusted as function of the tilt angle W.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for displaying position information relating to a position of a region of interest of a patient relative to an examination unit of an imaging apparatus, the method comprising:
   determining a first examination plane associated with the examination unit;
   mapping, via a lens of a camera disposed relative to the examination unit such that three non-collinear reference points lying in a first reference plane parallel to the first examination plane are mapped to three collinear first image points lying on a first line, one of the three non-collinear reference points is on a surface of an object on a positioning table and two of the three non-collinear reference points are on the positioning table;
   recording a camera image of the region of interest via the camera;
   displaying a positioning image, the positioning image showing the camera image; and
   displaying first marking information relating to a position of the first line in the positioning image.

2. The method of claim 1, further comprising:
   determining a second examination plane associated with the examination unit,
   mapping, via the lens of the camera, three non-collinear second reference points, lying in a second reference plane parallel to the second examination plane to three collinear second image points lying on a second line, and
   displaying second marking information relating to a position of the second line in the positioning image.

3. The method of claim 2, wherein at least one of
   the first marking information comprises a first marking line assigned to the first line and
   the second marking information comprises a second marking line assigned to the second line.

4. The method of claim 2, wherein an optical axis of the lens intersects at least one of the first line and the second line.

5. The method of claim 2, wherein the second examination plane is disposed at least one of perpendicular to and at a finite angle to the first examination plane.

6. The method of claim 2, wherein the examination unit includes an isocenter located in at least one of the first examination plane and the second examination plane.

7. The method of claim 2, wherein the examination unit includes a radiation source for producing radiation, wherein a central ray of the radiation lies in at least one of the first examination plane and the second examination plane.

8. The method of claim 2, further comprising:
   providing distance information relating to at least one of
      a first distance of the first reference plane from the first examination plane and
      a second distance of the second reference plane from the second examination plane.

9. A method for positioning a patient relative to an examination unit of an imaging apparatus, the method comprising:
   carrying out the method of claim 8, wherein the patient is placed in a preparatory position on a patient positioning device, wherein, in the preparatory position, at least one of a first slice of the region of interest of the patient lies in the first reference plane and a second slice of the region of interest of the patient lies in the second reference plane; and
   issuing a control command, the control command causing the patient to be transferred from the preparatory position to an examination position via the patient positioning device on the basis of the distance information, wherein, in the examination position, at least one of the first slice lies in the first examination plane and the second slice lies in the second examination plane.

10. The method of claim 1, wherein the examination unit includes an isocenter located in the first examination plane.

11. The method of claim 1, wherein the examination unit includes a radiation source for producing radiation, wherein a central ray of the radiation lies in the first examination plane.

12. The method of claim 1, further comprising:
   providing distance information relating to a first distance of the first reference plane from the first examination plane.

13. The method of claim 1, further comprising:
tilting the first examination plane by a tilt angle by tilting a tilt frame of the imaging apparatus and displaying the first marking information as a function of the tilt angle to compensate for the tilting.

14. An imaging apparatus, comprising:
an examination unit and a first examination plane associated with the examination unit;
a camera designed to capture a camera image of a region of interest of a patient, the camera being disposed relative to the examination unit such that, via a lens of the camera, three non-collinear reference points lying in a first reference plane parallel to the first examination plane are mappable to three collinear first image points lying on a first line, one of the three non-collinear reference points is on a surface of an object on a positioning table and two of the three non-collinear reference points are on the positioning table;
a positioning image display unit designed to display a positioning image, the positioning image showing the camera image; and
a first marking information display unit designed to display first marking information relating to a position of the first line in the positioning image.

15. The imaging apparatus of claim 14, wherein
a second examination plane is defined via the examination unit,
the camera is disposable relative to the examination unit such that, via a lens of the camera, three non-collinear second reference points lying in a second reference plane and parallel to the second examination plane are mappable to three collinear second image points lying on a second line, the imaging apparatus further comprising:
a second marking information display unit designed to display second marking information relating to a position of the second line in the positioning image.

16. The imaging apparatus of claim 15, further comprising:
a distance information providing unit designed to provide distance information relating to a distance of at least one of the first reference plane from the first examination plane and a distance of the second reference plane from the second examination plane; and
a control command issuing unit designed to issue a control command,
wherein the control command is configured to cause the patient to be transferred from a preparatory position to an examination position via a patient positioning device on the basis of the distance information,
wherein, in the preparatory position, at least one of a first slice of the region of interest lies in the first reference plane and a second slice of the region of interest lies in the second reference plane, and
wherein, in the examination position, at least one of the first slice lies in the first examination plane and the second slice lies in the second examination plane.

17. The imaging apparatus of claim 16, further comprising a patient positioning device designed to transfer the patient from the preparatory position to the examination position.

18. The imaging apparatus of claim 15, wherein at least one of
the first marking information comprises a first marking line assigned to the first line and
the second marking information comprises a second marking line assigned to the second line.

19. The imaging apparatus of claim 15, wherein the imaging apparatus is designed to carry out
recording a camera image of the region of interest via the camera;
displaying a positioning image, the positioning image showing the camera image; and
displaying first marking information relating to a position of the first line in the positioning image.

20. The imaging apparatus of claim 14, wherein the imaging apparatus is designed to carry out
recording a camera image of the region of interest via the camera;
displaying a positioning image, the positioning image showing the camera image; and
displaying first marking information relating to a position of the first line in the positioning image.

21. The imaging apparatus of claim 14, further comprising:
a distance information providing unit designed to provide distance information relating to a distance of the first reference plane from the first examination plane; and
a control command issuing unit designed to issue a control command,
wherein the control command is configured to cause the patient to be transferred from a preparatory position to an examination position via a patient positioning device on the basis of the distance information,
wherein, in the preparatory position, a first slice of the region of interest lies in the first reference plane, and
wherein, in the examination position, the first slice lies in the first examination plane.

22. The imaging apparatus of claim 21, further comprising a patient positioning device designed to transfer the patient from the preparatory position to the examination position.

23. The imaging apparatus of claim 14, wherein the imaging apparatus includes a tilting frame mounted to a tilting device so as to tilt the tilting frame relative to a fixed support frame of the imaging apparatus about a tilt axis.

* * * * *